United States Patent [19]
Lynch et al.

[11] Patent Number: 5,852,008
[45] Date of Patent: Dec. 22, 1998

[54] HETEROATOM SUBSTITUTED BENZOYL DERIVATIVES THAT ENHANCE SYNAPTIC RESPONSE MEDIATED BY RECEPTORS

[75] Inventors: Gary S. Lynch, Irvine; Gary A. Rogers, Santa Barbara, both of Calif.

[73] Assignee: The Regents of the University of California, Oakland, Calif.

[21] Appl. No.: 465,301

[22] Filed: Jun. 5, 1995

Related U.S. Application Data

[62] Division of Ser. No. 374,584, filed as PCT/US93/06916, Jul. 23, 1993.

[51] Int. Cl.[6] .......................... A61K 31/55; C07D 403/10
[52] U.S. Cl. .......................... 514/212; 514/321; 514/422; 540/607; 546/197; 548/526
[58] Field of Search ........................ 514/212, 321, 514/422; 540/607; 546/197; 548/526

[56] References Cited

U.S. PATENT DOCUMENTS

| | | | |
|---|---|---|---|
| 2,456,991 | 12/1948 | Prill | 549/462 |
| 2,487,179 | 11/1949 | Prill | 546/193 |
| 2,773,062 | 12/1956 | Prill | 548/462 |
| 3,869,431 | 3/1975 | Spiewak | 540/607 |
| 3,982,001 | 9/1976 | Heffe et al. | 548/462 |
| 4,025,629 | 5/1977 | Coverdale | 424/250 |
| 4,117,228 | 9/1978 | Tanaka et al. | 544/377 |
| 4,209,445 | 6/1980 | Oediger et al. | 546/245 |
| 4,209,446 | 6/1980 | Schulze et al. | 548/462 |
| 4,209,517 | 6/1980 | Riveron et al. | 548/462 |
| 4,333,938 | 6/1982 | Creuzet et al. | 546/245 |
| 4,369,139 | 1/1983 | Kyburz et al. | 548/539 |
| 4,425,327 | 1/1984 | Moller et al. | 424/65 |
| 4,431,662 | 2/1984 | Hodgson, Jr. | 548/543 |
| 4,438,142 | 3/1984 | Vinegar | 548/543 |
| 4,452,807 | 6/1984 | Aschwanden et al. | 548/544 |
| 4,499,100 | 2/1985 | Kluge et al. | 514/321 |
| 4,535,159 | 8/1985 | Forne et al. | 544/148 |
| 4,543,361 | 9/1985 | Muchowski et al. | 548/526 |
| 4,548,949 | 10/1985 | Muchowski et al. | 548/526 |
| 4,937,360 | 6/1990 | Liu et al. | 549/436 |
| 4,948,804 | 8/1990 | Galliani et al. | 548/539 |
| 5,196,439 | 3/1993 | Sugimoto et al. | 514/318 |
| 5,324,839 | 6/1994 | Clemence et al. | 546/174 |

FOREIGN PATENT DOCUMENTS

| | | |
|---|---|---|
| 0 451 626 A2 | 10/1991 | European Pat. Off. . |
| 1534547 | 7/1968 | France . |
| 2242978 | 4/1975 | France . |

OTHER PUBLICATIONS

Journal of Physiology, 424, pp. 533–543, 1990.
CA 104:10668d, 1986.
Chemical Abstracts, vol. 104, No. 2, 1986, Columbus, Ohio, US; Abstract No. 10668d, p. 324; col. 2.
Chemical Abstracts, vol. 88, No. 23, 1978, Columbus, Ohio, US; Abstract No. 169713n, p. 552; col. 2.
Chemical Abstracts, vol. 58, No. 38, 1963, Columbus, Ohio, US; Abstract No. 4541d, col. 4541.
Abdulla, Riaz F., *J. Heter. Chem.*, 10(3):347–351 (1973).
Abou–Ouf, A.A., et al., *Egypt. J. Pharm. Sci.*, 13(I):187–194 (1972).
Baudry, D., et al., *Tetrahedron Letters*, 54:4707–4710 (1970).
Baudry, D., et al., *Bulletin de la Societe Chimque de France*, 4:1413–1415 (1971) w/English abstract, see *Chemical Abstracts*, 75:300 No. 48308g (1971).
Cacchi, S., et al., *Tetrahedron Letters*, 27(33):3931–3934 (1986).
Gourdie, T.A., et al., *J. Med. Chem.*, 33:1177–1186 (1990).
Housny, A., et al., *Polymer Prepr.*, 27(1):120–121 (1986).
Ritter, D., et al., *Chem. Ber.*, 119:3704–3717 (1986).
Sam. Joseph, et al., *J. Pharm. Sci.*, 56(6):729–731 (1967).
Schwarz, G., et al., *Liebigs Ann. Chem.*, 1257–1270 (1981).
Tilly, G., *Chimie Therapeutique*, 1:57–65 (1967).

Primary Examiner—Yogendra N. Gupta
Attorney, Agent, or Firm—Townsend and Townsend and Crew LLP

[57] ABSTRACT

Compounds having the following structural formula,

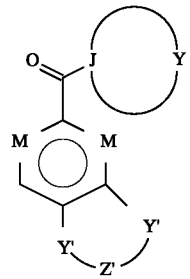

are useful for enhancing synaptic response mediated by AMPA receptors are disclosed, the invention compounds can also be used for the treatment of non-impaired subject for enhancing performance in sensory-motor and cognitive tasks which depend on brain networks utilizing AMPA receptor and for improving memory encoding.

10 Claims, 5 Drawing Sheets

HETEROATOM SUBSTITUTED BENZOYL DERIVATIVES THAT ENHANCE SYNAPTIC RESPONSE MEDIATED BY RECEPTORS

This is a Division of application Ser. No. 08/374,584, filed Jan. 24, 1995, which is a 371 of PCT/US93/06916, filed Jul. 23, 1993.

ACKNOWLEDGEMENT

This invention was made with United States Government support under Grant No. AFOSR 89-0383, awarded by the Air Force Office of Scientific Research. The United States Government has certain rights in the invention in the United States.

FIELD OF INVENTION

The present invention relates to novel compounds which are useful, for example, in the prevention of cerebral insufficiency, to enhance receptor functioning in synapses in those brain networks responsible for higher order behaviors, and the like. In a particular aspect, the invention relates to methods for the use of the compounds disclosed herein, and to methods for the preparation thereof.

BACKGROUND OF THE INVENTION

Excitatory synaptic currents at many (probably most) sites in telencephalon (cortex, limbic system, striatum; about 90% of human brain) and cerebellum occur when the transmitter glutamate is released by input axons onto what are usually referred to as the β-amino-3-hydroxy-5-methyl-isoxazole-4-propionic acid (AMPA), or AMPA/quisqualate, receptors. Drugs that enhance these receptor currents will facilitate communication in brain networks responsible for perceptual-motor integration and higher order behaviors. It is also known from the literature [see Arai and Lynch in Brain Research, in press] that such drugs will promote the formation of long-term potentiation, a physiological effect widely held to encode memory.

For example, Ito et al., J. Physiol. Vol. 424:533–543 (1990), discovered that aniracetam, N-anisoyl-2-pyrrolidinone, enhances AMPA receptor mediated currents without affecting currents generated by other classes of receptors. Unfortunately, however, the drug is effective only at high concentrations (~1.0 mM) applied directly to the brain. The low potency, limited solubility, and peripheral metabolism of aniracetam limit its utility as an experimental tool and its potential value as a therapeutic. There is a need, therefore, for the design and synthesis of new drugs that are more potent, more soluble and less readily metabolized than aniracetam. Such compounds would provide new tools for manipulating the properties of the AMPA receptor and would be a major step towards a drug that could enhance AMPA receptor function in the brain after peripheral administration.

BRIEF DESCRIPTION OF THE INVENTION

We have discovered novel compounds that are several times more potent than aniracetam in enhancing synaptic responses (i.e, they produce larger effects than aniracetam at lower concentrations). The invention compounds increase the strength of long-term potentiation and increase synaptic responses in the brain following peripheral administration. Invention compounds can be used, for example, to facilitate behaviors dependent upon AMPA receptor, as therapeutics in conditions in which receptors or synapses utilizing them are reduced in numbers, and the like.

DETAILED DESCRIPTION OF THE INVENTION

Figure 1B:
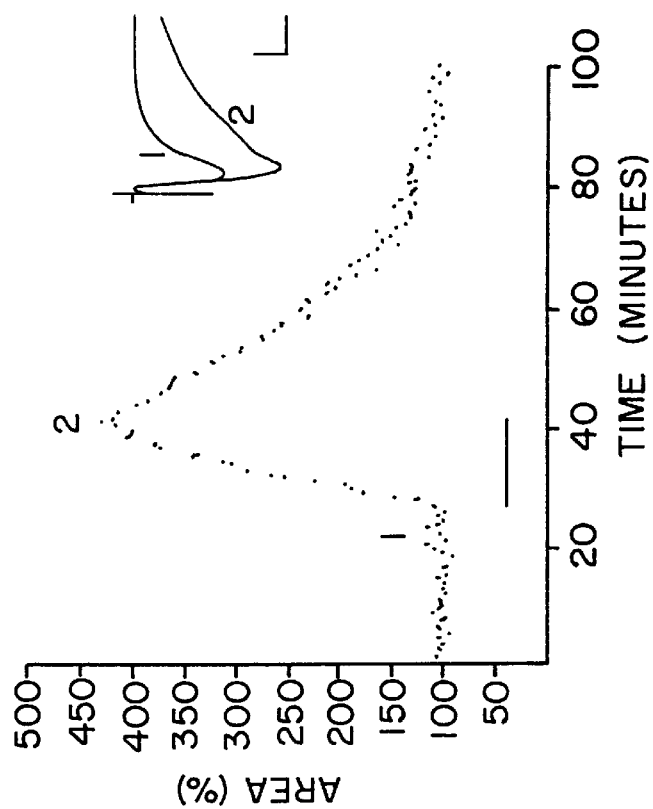
FIG. 1 shows that Invention Compound I (1-(1,4-benzodioxan-5-ylcarbonyl)-1,2,3,6-tetrahydropyridine; alternatively referred to as N-(3,4-ethylenedioxy)benzoyl-1,2,3,6-tetrahydropyridine) increases the amplitude and duration (measured as half-width) of synaptic responses in the field CA1 in in vitro slices prepared from rat hippocampus. These responses are known to be mediated by AMPA receptors [Muller et al., Science Vol. 242: 1694–1697 (1988)]. Note that Invention Compound I at 750 μM has a much larger effect than does aniracetam at twice the concentration (1500 μM). Note also that the effects occur quickly after infusion (horizontal bar) and reverse upon washout.

Release of glutamate at synapses at many sites in mammalian forebrain stimulates two classes of postsynaptic receptors usually referred to as AMPA/quisqualate and N-methyl-D-aspartic acid (NMDA) receptors. The first of these mediates a voltage independent fast excitatory postsynaptic current (the fast epsc) while the NMDA receptor generates a voltage dependent, slow excitatory current. Studies carried out in slices of hippocampus or cortex indicate that the AMPA receptor-mediated fast epsc is by far the dominant component at most glutaminergic synapses under most circumstances. AMPA receptors are not evenly distributed across the brain but instead are largely restricted to telencephalon and cerebellum. They are found in high concentrations in the superficial layers of neocortex, in each of the major synaptic zones of hippocampus, and in the striatal complex [see, for example, Monaghan et al., in Brain Research 324:160–164 (1984)]. Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that enhance the functioning of the AMPA receptor could have significant benefits for intellectual performance. Such drugs should also facilitate memory encoding. Experimental studies (see, for example, Arai and Lynch, Brain Research, in press) indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

There is a considerable body of evidence showing that LTP is the substrate of memory; for example, compounds that block LTP interfere with memory formation in animals, and certain drugs that disrupt learning in humans antagonize the stabilization of LTP [see, for example, del Cerro and Lynch, Neuroscience 49:1–6 (1992)]. Recently, Ito et al. (1990) supra, uncovered a possible prototype for a compound that selectively facilitates the AMPA receptor. These authors found that the nootropic drug aniracetam (N-anisoyl-2-pyrrolidinone) increases currents mediated by brain AMPA receptors expressed in Xenopus oocytes without affecting responses by γ-amino-butyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effects on NMDA-receptor mediated potentials [see, for example, Staubli et al., in Psychobiology 18:377–381 (1990) and Xiao et al., in Hippocampus 1:373–380 (1991)]. Aniracetam has also been found to have an extremely rapid onset and washout, and can be applied repeatedly with no apparent lasting effects; these are valuable traits for behaviorally-relevant drugs.

Without wishing to be bound by any particular theory of action, it is presently believed to be likely that the major effect of aniracetam is to slow the unusually rapid rate at which AMPA receptors desensitize. The compound also greatly prolongs synaptic responses. This would be expected if it increased the mean open time of AMPA receptor channels by delaying desensitization. Indeed, it has been found that aniracetam prolongs the open time of AMPA receptor responses and blocks their desensitization in membrane patches excised from hippocampal neurons in culture; the magnitude of the effect corresponds closely to the increase in the duration of synaptic responses (recorded in culture or slices) produced by the drug [Tang et al., Science 254: 288–290 (1991)]. Aniracetam may also produce other changes in receptor properties; it causes a small but reliable decrease in the binding of agonists (but not antagonists) to the receptor [Xiao et al., 1991, supra] and may also slightly enhance the conductance of the receptor channel [Tang et al. supra].

Aniracetam is classified as a nootropic drug. Nootropics are proposed to be "cognitive enhancers" [see Fröstl and Maitre, Pharmacopsychiatry Vol. 22:54–100 (Supplement) (1989)] but their efficacy in this regard is highly controversial. Several nootropics have been tested in slices [see, for example, Olpe et al., Life Sci. Vol. 31:1947–1953 (1982); Olpe et al., Europ. J. Pharmacol. Vol. 80:415–419 (1982); Xiao et al., 1991, supra] and only aniracetam and its near relative (R)-1-p-anisoyl-3-hydroxy-2-pyrrolidinone (AHP) facilitate AMPA receptor mediated responses. Hence, whatever effects the nootropics might have are not mediated by facilitation of fast epsc. It is also the case that peripheral administration of aniracetam is not likely to influence brain receptors. The drug works only at high concentrations (~1.0 mM) and about 80% of it is converted to anisoyl-GABA following peripheral administration in humans [Guenzi and Zanetti, J. Chromatogr. Vol. 530:397–406 (1990)]. The metabolite, anisoyl-GABA, has been found to have no aniracetam-like effects.

The conversion of aniracetam to anisoyl-GABA involves a break in the pyrrolidinone ring between the nitrogen and the adjacent carbonyl group, as illustrated below:

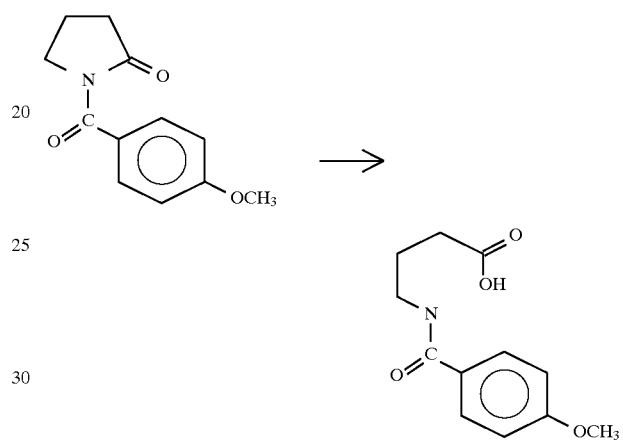

In order to overcome the stability problems with aniracetam, and in efforts to provide compounds with improved physiological activity, we have developed a number of compounds having such improved properties.

Therefore, in accordance with the present invention, there are provided novel compounds having the structure:

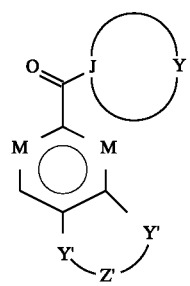

wherein:

—Y— is selected from:

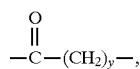

wherein y is 3, 4, or 5; or

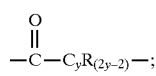

when —J— is selected from:

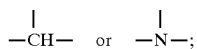

or
—(CR$_2$)$_x$—, wherein x is 4, 5, or 6,
—C$_x$R$_{(2x-2)}$—, when —J— is:

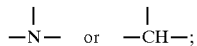

—R is hydrogen or a straight chain or branched chain alkyl group having 1–6 carbon atoms;
each —M— is independently selected from:
  —C(H)—, or
  —C(Z)—, wherein Z is selected from:
    —R or
    —OR;
  wherein M can optionally be linked to Y by a linking moiety selected from —C$_{n'}$H$_{2n'}$—, —C$_{n'}$H$_{(2n'-1)}$—, —O— or —NR—, wherein n' is 0 or 1;
each —Y'— is independently selected from:
  —O—,
  —NR— or
  —N=; and
—Z'— is selected from:
  —(CR$_2$)$_z$—, wherein z is 1, 2, or 3, or
  —C$_{z'}$R$_{(2z'-1)}$—, wherein z' is 1 or 2, when one —Y'— is —N=, or
  —C$_2$R$_2$— when both —Y'— are —N= or both —Y'— are —O—;
with the proviso that when each M is —C(H)—, each Y' is —O—, and Z' is —CH$_2$—, then Y is not —(CH$_2$)$_{4,5}$—; or

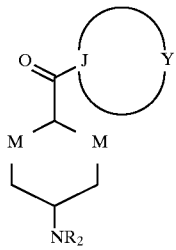

wherein:
—Y—,

and —M— are as defined above, or

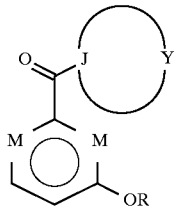

wherein:
—Y—,

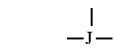

and —M— are as defined above.

In a presently preferred embodiment of the present invention, —Y— is selected from:
—(CH$_2$)$_x$—, wherein x is 4 or 5,
—C$_x$H$_{(2x-2)}$—, wherein x is 4 or 5, or

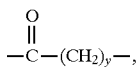

wherein y is 3 or 4.

In another presently preferred embodiment of the present invention, Z' is selected from —CR$_2$—, —CR$_2$—CH$_2$—, —CR=, or —CR=CH—, wherein each R is independently H or a straight chain or branched chain alkyl group having 1–6 carbon atoms, as defined above.

In still another presently preferred embodiment of the present invention,

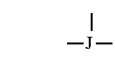

is

In yet another presently preferred embodiment of the present invention, each Y' is —O—, and Z' is —CH$_2$— or —CH$_2$—CH$_2$—. This pattern of substitution is especially preferred when —Y— is selected from one of the preferred groups set forth above.

When the aromatic ring is not further substituted with a fused heterocyclic ring, preferred substituent —NR$_2$ (i.e., where the ring bears a para-substituent) is —NH(CH$_3$) or —N(CH$_3$)$_2$, while preferred substituent —OR (i.e., where the ring bears a meta-substituent) is —OCH$_3$.

Especially preferred compounds of the present invention have the following structures:

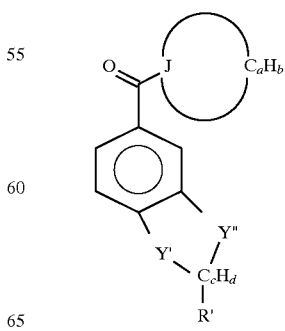

wherein

is

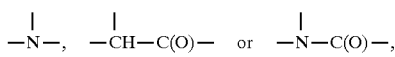

Y' is O, N or NR', Y", when present, is O, N or NR', R' is H or a straight chain or branched chain alkyl group having 1–4 carbon atoms, a=3, 4, 5 or 6, b=an even number between 6–12, inclusive, depending on the value of "a", c=1 or 2, d=0, 1 or 3, or the combination of Y' and $C_cH_d$—R' produces a dialkylamino derivative thereof (wherein a dialkylamino group replaces the heterocyclic ring fused to the core aromatic ring).

A specific example of a presently preferred compound is 1-(1,4-benzodioxan-5-ylcarbonyl)-1,2,3,6-tetrahydropyridine (referred to herein as Invention Compound I), is shown below:

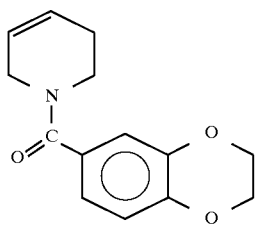

(I)

Another example of a presently preferred compound is (1-(1,3-benzodioxol-5-ylcarbonyl)-piperidine) (referred to herein as Invention Compound II), shown below:

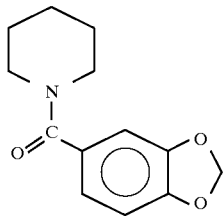

(II)

A variant of Invention Compounds I and II, in which the nitrogen-containing heterocycle is replaced with a cyclopentanone or cyclohexanone ring, is expected to be especially metabolically stable and can be synthesized as follows:

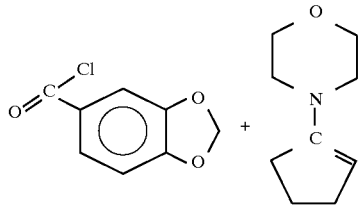

(IV)

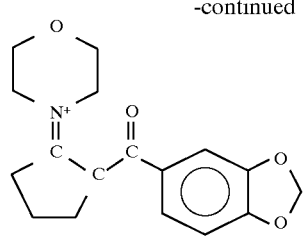

 $H_3O^+$

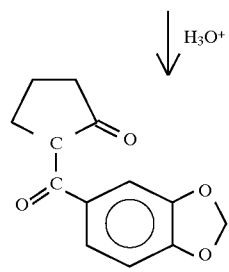

The above compound is referred to herein as Invention Compound IV. $EC_{50}$ data for this and a number of other compounds described herein have been determined and are presented in the Examples. Additional preferred compounds of the invention include Invention Compound V (i.e., (R,S) -1-(2-methyl-1,3-benzodioxol-5-ylcarbonyl)-piperidine, Invention Compound XIV (i.e., 1-(quinoxalin-6-ylcarbonyl) -piperidine, Invention Compound XV (i.e., N-(4-dimethylamino)benzoyl-1,2,3,6-tetrahydropyridine, and the like.

In accordance with another embodiment of the present invention, there are provided methods for the preparation of the above-described compounds. One such method comprises:

(a) contacting a benzoic acid derivative under conditions suitable to activate the carboxy group thereof for the formation of an amide therefrom. This is accomplished, for example, by activating the acid with carbonyl diimidazole, by producing the corresponding benzoyl chloride derivative, and the like. The benzoic acid derivative employed for the preparation of the above-described compounds typically has the structure:

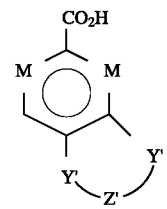

wherein —M—, —Y'—, and Z' are as defined above; or

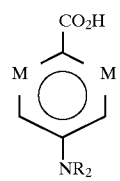

wherein —M— and —R are as defined above; or

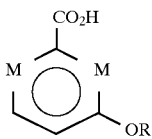

wherein —Y—, —M— and —A' are as defined above; and (b) contacting the activated benzoic acid derivative produced in step (a) with a nitrogen-containing heterocyclic compound of the structure:

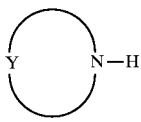

wherein Y is as defined above, wherein said contacting is carried out under conditions suitable to produce the desired imides or amides (i.e., aniracetam-like compounds).

Conditions suitable for activating the carboxy group of the benzoic acid (i.e., for the formation of an amide therefrom) can readily be determined by those of skill in the art. For example, the benzoic acid can be contacted with carbonyl diimidazole (see, for example, Paul and Anderson in J. Am. Chem. Soc. 82:4596 (1960)), a chlorinating agent (such as thionyl chloride or oxalyl chloride), or the like, under conditions suitable to produce an activated acid, such as the corresponding benzoyl chloride derivative. See, for example, March, *Advanced Organic Chemistry: Reactions, Mechanisms and Structure*, McGraw-Hill, Inc. 1968.

Suitable reaction conditions used to carry out the step (b) condensation are well known to those of skill in the art. The artisan also recognizes that care, is generally taken to carry out such reactions under substantially anhydrous conditions.

Another method for the preparation of the compounds of the present invention comprises:

(a) contacting a benzoic acid derivative (as described above) with at least two equivalents of a suitable base in suitable solvent, then contacting the resulting ionized benzoic acid derivative with pivaloyl chloride or a reactive carboxylic acid anhydride under conditions suitable to produce a mixed anhydride containing said benzoic acid; and (b) contacting s aid mixed anhydride produced in step (a) with a nitrogen-containing heterocyclic compound (as described above), wherein said contacting is carried out under conditions suitable to produce the desired imides or amides (i.e., aniracetam-like compounds).

Suitable bases contemplated for use in this embodiment of the present invention include tertiary amine bases such as triethyl amine, and the like. Suitable solvents contemplated for use in the practice of the present invention include inert solvents such as $CH_2Cl_2$, alcohol-free $CHCl_3$, and the like. Reactive carboxylic acid anhydrides contemplated for use in the practice of the present invention include trifluoroacetic anhydride, trichloroacetic anhydride, and the like.

Suitable reaction conditions used to carry out the above-described reaction are well known to those of skill in the art. The artisan also recognizes that care is generally taken to carry out such reactions under substantially anhydrous conditions.

Yet another suitable method for the preparation of the compounds of the present invention comprises:

(a) contacting 3,4-(alkylenedihetero)-benzaldehyde with ammonia under conditions suitable to form an imine derivative thereof, (b) contacting the imine produced in step (a) with:

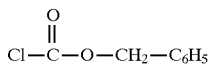

under conditions suitable to form a benzyloxycarbonyl (BOC) imine, (c) contacting the product of step (b) with a simple conjugated diene such as butadiene under cycloaddition reaction conditions; and (d) contacting the reaction product of step (c) with a Lewis acid under conditions suitable for Friedel-Crafts acylation to occur.

3,4-(alkylenedihetero)benzaldehydes contemplated for use in the practice of the present invention include 3,4-(methylenedioxy)benzaldehyde, 3,4-(ethylenedioxy)benzaldehyde, 3,4-(propylenedioxy)benzaldehyde, 3,4-(ethylidenedioxy)benzaldehyde, 3,4-(propylenedithio)benzaldehyde, 3,4-(ethylidenethioxy)benzaldehyde, 4-benzimidazolecarboxaldehyde, 4-quinoxalinecarboxaldehyde, and the like.

Simple conjugated dienes contemplated for use in the practice of the present invention include butadiene, 1,3-pentadiene, isoprene, and the like.

Lewis acids contemplated for use in the practice of the present invention are well known in the art and include $AlCl_3$, $ZnCl_2$, and the like. See, for example, March, supra.

Still another suitable method for the preparation of the compounds of the present invention comprises:

(a) contacting 2,3-dihydroxy naphthalene with 1,2-dibromoethane in the presence of base under conditions suitable to produce an ethylenedioxy derivative of naphthalene, (b) contacting the ethylenedioxy derivative of naphthalene produced in step (a) with a suitable oxidizing agent under conditions suitable to produce 4,5-ethylenedioxyphthaldehydic acid, (c) contacting the product of step (b) with anhydrous ammonia under conditions suitable to form an imine, which is then treated with a suitable carbonyl-activating agent (e.g., a carbodiimide such as dicyclohexylcarbodiimide) under cyclization conditions suitable to form an acyl imine, and (d) contacting the product of step (c) with a simple conjugated diene under conditions suitable for cycloaddition to occur.

Suitable oxidizing agents contemplated for use in the practice of the present invention include potassium permanganate, and the like. Oxidizing conditions suitable to produce 4,5-ethylenedioxyphthaldehydic acid are described, for example, in Organic Synthesis, Collective Volume 2, at page 523 (1943).

Treatment of 4,5-ethylenedioxyphthaldehydic acid with anhydrous ammonia initially forms an imine, which is then treated with a suitable carbonyl-activating agent which, under appropriate reaction conditions, promotes cyclization of the intermediate imine to produce an acyl imine.

Suitable reaction conditions used to carry out the above-described reactions are well known to those of skill in the art. The artisan also recognizes that care is generally taken to carry out such reactions under substantially anhydrous conditions.

In accordance with yet another embodiment of the present invention, there are provided methods for enhancing synaptic responses mediated by AMPA receptors. The method comprises administering to a subject an effective amount of a compound having the structure:

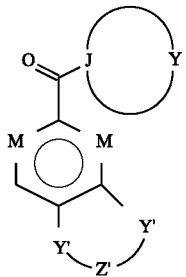

wherein:
—Y— is selected from:

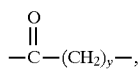

wherein y is 3, 4, or 5; or

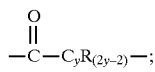

when —J— is selected from:

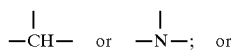

or
—(CR$_2$)$_x$—, wherein x is 4, 5, or 6,
—C$_x$R$_{(2x-2)}$—, when —J— is:

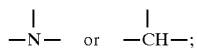

—R is hydrogen or a straight chain or branched chain alkyl group having 1–6 carbon atoms;
each —M— is independently selected from:
  —C(H)—, or
  —C(Z)—, wherein Z is selected from:
    —R, or
    —OR;
    wherein M can optionally be linked to Y by a linking moiety selected from —C$_{n'}$H$_{2n'}$—, —C$_{n'}$H$_{(2n'-1)}$—, —O— or —NR—, wherein n' is 0 or 1;
each —Y'— is independently selected from:
  —O—,
  —NR— or
  —N=; and
—Z'— is selected from:
  —(CR$_2$)$_z$—, wherein z is 1, 2, or 3, or
  —C$_{z'}$R$_{(2z'-1)}$—, wherein z' is 1 or 2, when one —Y'— is —N=, or
  —C$_2$R$_2$— when both —Y'— are —N= or both —Y'— are —O—; or

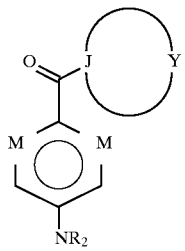

wherein:
—Y— and —M— are as defined above, or

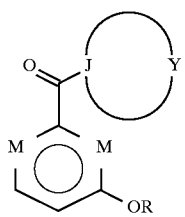

wherein:
—Y— and —M— are as defined above.

Invention compounds are demonstrated in the examples which follow to be substantially more potent than aniracetam in increasing AMPA receptor function in slices of hippocampus. For example, Invention Compound I is shown to facilitate induction of maximal long-term potentiation in vitro, and to reversibly prolong synaptic responses in the hippocampus following peripheral (i.e., intraperitoneal) injections in anesthetized rats.

The above-described compounds can be incorporated into a variety of formulations (e.g., capsule, tablet, syrup, suppository, injectable form, etc.) for administration to a subject. Similarly, various modes of delivery (e.g., oral, rectal, parenteral, intraperitoneal, etc.) can be employed. Dose levels employed can vary widely, and can readily be determined by those of skill in the art. Typically, amounts in the milligram up to gram quantities are employed. Subjects contemplated for treatment with the invention compounds include humans, domesticated animals, laboratory animals, and the like.

Invention compounds can be used, for example, as a research tool for studying the biophysical and biochemical properties of the AMPA receptor and the consequences of selectively enhancing excitatory transmission on the operation of neuronal circuitry. Since invention compounds reach central synapses, they will allow for testing of the behavioral effects of enhancing AMPA receptor currents.

Metabolically stable variants of aniracetam have many potential applications in humans. For example, increasing the strength of excitatory synapses could compensate for losses of synapses or receptors associated with aging and brain disease (e.g., Alzheimer's). Enhancing AMPA receptors could cause more rapid processing by multisynaptic circuitries found in higher brain regions and thus could produce an increase in perceptual-motor and intellectual performance. As another example, since increasing AMPA receptor-mediated responses facilitates synaptic changes of the type believed to encode memory, metabolically stable variants of aniracetam are expected to be functional as memory enhancers.

Additional applications contemplated for the compounds of the present invention include improving the performance of subjects with sensory-motor problems dependent upon brain networks utilizing AMPA receptors; improving the performance of subjects impaired in cognitive tasks dependent upon brain networks utilizing AMPA receptors; improving the performance of subjects with memory deficiencies; and the like.

Accordingly, invention compounds, in suitable formulations, can be employed for decreasing the amount of time needed to learn a cognitive, motor or perceptual task. Alternatively, invention compounds, in suitable formulations, can be employed for increasing the time for which cognitive, motor or perceptual tasks are retained. As another alternative, invention compounds, in suitable formulations, can be employed for decreasing the quantity and/or severity of errors made in recalling a cognitive, motor or perceptual task. Such treatment may prove especially advantageous in individuals who have suffered injury to the nervous system, or who have endured disease of the nervous system, especially injury or disease which affects the number of AMPA receptors in the nervous system. Invention compounds are administered to the affected individual, and thereafter, the individual is presented with a cognitive, motor or perceptual task.

The invention will now be described in greater detail by reference to the following non-limiting examples.

EXAMPLES

Example I

Preparation of (R,S)-1-(2-methyl-1,3-benzodioxol-5-ylcarbonyl)-piperidine (V)

The synthesis of 2-methyl-1,3-benzodioxole is conducted by the procedure of Nichols and Kostuba (J. Med. Chem 22:1264 (1979)). A solution of 10.3 g (76 mmol) of 2-methyl-1,3-benzodioxole and 21 ml of acetic anhydride is treated with 3.5 ml $BF_3$ etherate at 0° C. for 24 hr and at −20° C. for three days. The reaction solution is poured into 250 ml 1M $Na_2CO_3$ and extracted with ether. The ether is dried over $Na_2SO_4$, then removed under reduced pressure. Purification and distillation under reduced pressure yields the ketone, 5-acetyl-2-methyl-1,3-benzodioxole.

The above-described ketone is oxidized to the acid by dissolution in aqueous dioxane/NaOH and treatment with $Br_2$ and iodoform reagent ($KI/I_2$ in aqueous NaOH). Excess halogen is destroyed with $Na_2SO_3$ and the aqueous solution extracted with $CH_2Cl_2$, then ether. Acidification of the aqueous solution with conc. HCl yields 2-methyl-1,3-benzodioxol-5-ylcarboxylic acid, which can be crystallized from $CHCl_3/CCl_4$/petroleum ether. $^1$H NMR δ 1.71 (d, 3, J=5 Hz), 6.36 (q, 1, J=5 Hz), 6.81 (d, 1, J=8.2 Hz), 7.46 (d, 1, J=1.6 Hz), and 7.71 ppm (dd, 1, J=1.6, 8.2 Hz).

The above-described acid is coupled to piperidine by first activating the acid with a suitable reagent. Specifically, the acid is suspended in $CH_2Cl_2$ and stirred with one equivalent carbonyl diimidazole (CDI). After 30 min, 10% excess piperidine is added. After the reaction is complete (usually less than 1 hr), the solution is extracted with aqueous HCl, water, and aqueous $NaHCO_3$. The organic solution is dried over $Na_2SO_4$ and $CH_2Cl_2$ removed under reduced pressure. Crystallization of the resulting oil by methods known in the art gives (R,S)-1-(2-methyl-1,3-benzodioxol-5-ylcarbonyl)-piperidine (V) as a white solid. $^1$H NMR δ 1.5–1.7 (br m, 6), 1.68 (d, 3, J=5.0 Hz), 6.29 (q, 1, J=4.9 Hz), 6.75 (d, 1, J=7.9 Hz), 6.84 (d, 1, J=0.93 Hz), and 6.88 (dd, 1, J=8.0, 1.0 Hz).

Example II

Alternate synthesis of (R,S)-1-(2-methyl-1,3-benzodioxol-5-ylcarbonyl)-piperidine (V)

Catechol (11.0 g; 0.100 mol) is dissolved in 50 ml of ether and 29 g of freshly-prepared dioxane dibromide (Yanovskaya, Terent'ev and Belsn'kii), J. Gen. Chem. Vol. 22:1594 (1952)) is added slowly as a solution in 50 ml of ether. The organic solution is washed with water (3 times) and dried over $MgSO_4$. The solvent is removed under reduced pressure to yield 4-bromocatechol as a red-brown oil. $^1$H NMR δ 5.52 (s, 1), 5.70 (s, 1), 6.74 (d, 1, J=8.74 Hz), 6.92 (dd, 1, J=8.3, 2.3 Hz), and 7.01 ppm (d, 1, J=2.6 Hz).

4-Bromocatechol (18.9 g, 0.100 mol) is dissolved in 200 ml dry toluene and 20 ml vinyl acetate is added at once, followed by 0.20 g mercuric oxide and 0.4 ml $BF_3$ etherate. After standing for 10 hr, the solution is extracted with 0.5M NaOH until the aqueous layer is strongly basic (pH>12). The organic solution is dried over $K_2CO_3$ and filtered to remove the drying agent. Removal of the toluene under reduced pressure and treatment of the resulting oil with silica gel in petroleum ether (low boiling) gives 18 g of (R,S)-5-bromo-2-methyl-1,3-benzodioxole as a yellow oil, $^1$H NMR δ 1.67 (d, 1, J=4.78 Hz), 6.27 (q, 1, J=4.72 Hz), 6.63 (d, 1, J=8.11 Hz), and 6.88–6.93 ppm (m, 2).

Conversion of the bromoaromatic derivative to the substituted benzoic acid is accomplished by the well-known Grignard reaction (or other suitable method known in the art). Specifically, the bromoderivative is dissolved in dry tetrahydrofuran and combined with magnesium. The resulting Grignard reagent is treated with gaseous carbon dioxide. The reaction solution is quenched with aqueous HCl and the product acid is extracted into ether. The ether solution is extracted with aqueous bicarbonate and the bicarbonate solution is then washed with ether or other suitable organic solvent. The bicarbonate solution is neutralized with conc. HCl to yield 2-methyl-1,3-benzodioxol-5-ylcarboxylic acid, which can be crystallized from $CHCl_3/CCl_4$/petroleum ether, as described above. The acid is then coupled to piperidine as described above, to produce the desired product.

Example III

Synthesis of 1-(1,4-benzodioxan-5-ylcarbonyl)-1,2,3,6-tetrahydropyridine (I)

1,4-benzodioxan-6-carboxylic acid (also known as 3,4-ethylenedioxybenzoic acid) was synthesized by the oxidation of commercially available 3,4-ethylenedioxybenzaldehyde with potassium permanganate, as described in Org. Syn. 2:538 (1943).

1,4-benzodioxan-6-carboxylic acid (3.0 g; 16.7 mmol) was suspended in 40 mL of dichloromethane. The acid dissolved upon addition of 3.7 g (2.2 equivalents) of triethylamine. Addition of 2.0 g of pivaloyl chloride was exothermic, and produced a dense precipitate. The mixture was stirred at room temperature for about 20 minutes, then 1.52 g of 1,2,3,6-tetrahydropyridine was slowly added.

Product was purified by diluting the reaction mixture with an equal volume of diethyl ether, followed by sequential extractions with 1) 1M HCl, 2) aqueous sodium bicarbonate, and 3) aqueous sodium carbonate. The organic solution was dried over sodium sulfate and potassium carbonate. Removal of solvent on a rotary evaporator gave 4.07 g of a pale yellow, viscous oil. Electron impact mass spectroscopy (EIMS) showed the parent ion at an m/z value of 245, and a base peak at 163 for the acylium ion. Nuclear magnetic resonance spectroscopy (NMR) at 500 MHz revealed resonances at 6.97 (1H, d, J=1.81); 6.93 (1H, dd, J=8.23, 1.86); 6.87 (1H, d, J=8.23); 5.5–5.9 (2H, m); 4.27 (4H, s); 3.4–4.3 (4H, m); and 2.2 ppm (2H, br s), relative to TMS.

Example IV

Alternate synthesis of 1-(1,4-benzodioxan-5-ylcarbonyl)-1,2,3,6-tetrahydropyridine (I)

Synthesis is performed in the same manner as described for the preparation of Invention Compound VIII with substitution of 1,2,3,6-tetrahydropyridine for 3-pyrroline. EIMS m/z=245 (parent), 163 (base), 35, and 107. $^1$H NMR δ 2.2 (br s, 2), 3.4–4.3 (m, 4), 4.27 (s, 4), 5.5–5.9 (m, 2), 6.87 (d, 1, J=8.23 Hz), 6.93 (dd, 1, J=8.23, 1.86 Hz), and 6.97 ppm (d, 1, 1.81 Hz). $^{13}$C NMR δ 64.27 and 64.44 (—OCH$_2$CH$_2$O—) and 170.07 ppm (carbonyl).

Example V

Preparation of 1-(1,3-benzodioxol-5-ylcarbonyl)-1,2,3,6-tetrahydro-pyridine (III)

The product amide is made by the method employed for the preparation of Invention Compound V, which uses carbonyl diimidazole in order to activate piperonylic acid, or piperonyloyl chloride (available from Aldrich) can be combined with 1,2,3,6-tetrahydropyridine either in a suitable anhydrous solvent or without solvent. In either case, the isolation of product is performed in the same manner as done for Invention Compound V to give Invention Compound III as a white solid. EIMS m/z=231 (parent, 149 (base), and 121. $^1$H NMR δ 2.21 (br s, 2), 3.4–4.3 (br m, 4), 5.87 (m, 2), 6.00 (s, 2), 6.83 (d, 1, J=7.84 Hz), and 6.92–6.96 (dd and d, 2). $^{13}$C NMR δ 101.3 (—OCH$_2$O—) and 169.9 ppm (carbonyl).

Example VI

Preparation of 1-(1,3-benzodioxol-5-ylcarbonyl)-hexamethyleneimine (VII)

The product amide is made by the same method as employed for the preparation of Invention Compound V, which uses carbonyl diimidazole in order to activate piperonylic acid, or piperonyloyl chloride can be combined with hexamethyleneimine in a suitable anhydrous solvent or without solvent. In either case, the isolation of product is performed in the same manner as done for Invention Compound V to yield Invention Compound VII as a colorless oil. $^1$H NMR δ 1.6 (br m, 6), 1.83 (br m, 2), 3.4 (br m, 2), 3.63 (br m, 2), 5.98 (s, 2), and 6.78–6.9 (m, 3).

Example VII

Preparation of 1-(1,4-benzodioxan-5-ylcarbonyl)-3-pyrroline (VIII)

1,4-Benzodioxan-6-carboxaldehyde is oxidized to the corresponding acid by the procedure of Shriner and Kliederer in Organic Syntheses, Coll. Vol. 2:538 (1943). Coupling of the acid with 3-pyrroline is conducted by employing the same method as employed for the preparation of Invention Compound V, which uses carbonyl diimidazole in order to activate the carboxylic acid, or any other method known in the art, such as, for example, activation by the reaction of the triethylammonium salt with trimethylacetyl chloride. The product is crystallized from CCl$_4$/Et$_2$O/ hexanes. EMIS m/z=231 (parent), 163 (base), 135, and 107. $^1$H NMR δ 4.25–4.30 (m, 6), 4.43 (br, 2), 5.75 (m, 1), 5.85 (m, 1), 6.88 (d, 1, J=8.42 Hz), 7.06 (dd, 1, J=8.38, 2.03 Hz), and 7.09 (d, 1, J=2.05 Hz).

Example VIII

Preparation of 1-(1,3-benzoxazol-6-ylcarbonyl)-1,2,3,6-tetrahydropyridine (IX)

3-Amino-4-hydroxybenzoic acid (1.0 g; 6.5 mmol) is suspended in 3 ml diethoxymethyl acetate and heated to reflux for 45 min. The cooled solution is diluted with ether and 1.02 g of 1,3-benzoxazol-6-carboxylic acid is collected by filtration. EMIS m/z=163 (parent), 146 (base), and 118.

Coupling of 1,3-benzoxazol-6-carboxylic acid with 1,2,3,6-tetrahydropyridine is performed in the same manner as described for the preparation of Invention Compound V through activation with carbonyl diimidazole or by activation with other suitable reagents such as oxalyl chloride. The product can be isolated by the same methods as described for the isolation of Invention Compound V and purified by chromatography on silica gel. EIMS m/z=228 (parent), 146 (base), and 118. $^1$H NMR δ 2.2 (br, 2), 3.4–4.3 (br m, 4), 5.7–5.95 (br m, 2), 7.52 (dd, 1, J=8.39, 1.49 Hz), 7.64 (d, 1, J=8.41 Hz), 7.87 (d, 1, J=1.32 Hz), and 8.16 ppm (s, 1).

Example IX

Preparation of 1-(1,3-benzoxazol-6-ylcarbonyl)-piperidine (X)

The amide is prepared by coupling 1,3-benzoxazol-6-carboxylic acid with piperidine by activation of the acid with carbonyl diimidazole as described for the preparation of Invention Compound V. Dilution of the reaction solution with more CH$_2$Cl$_2$ causes the product to precipitate. Purification is achieved by chromatography on silica gel. EMIS m/z=230 (parent), 229, 146 (base), and 118. $^1$H NMR δ 1.55 (br m, 4), 1.70 (br, 2), 3.4 (br, 2), 3.75 (br, 2), 7.48 (dd, 1, J=8.29, 1.22 Hz), 7.62 (d, 1, J=8.44 Hz), 7.84 (d, 1, J=1.00 Hz), and 8.15 ppm (s, 1).

Example X

Preparation of 1-(1,3-benzoxazol-5-ylcarbonyl)-1,2,3,6-tetrahydropyridine (XI)

4-Amino-3-hydroxybenzoic acid is converted into 1,3-benzoxazol-5-carboxylic acid by treating with diethoxymethyl acetate as described for the preparation of Invention Compound IX. EMIS m/z=163 (parent), 146 (base), 118, 90, and 63. Coupling of the acid with 1,2,3,6-tetrahydropyridine is performed in the same manner as described for the preparation of isomeric Invention Compound IX. $^1$H NMR δ 2.1–2.4 (br, 4), 3.4–4.3 (br m, 4), 5.5–5.95 (br m, 2), 7.45 (dd, 1, J=8.17, 1.41 Hz), 7.70 (d, 1, J=0.96 Hz), 7.83 (d, 1, J=8.16 Hz), and 8.18 ppm (s, 1).

Example XI

Preparation of 1-(1,3-benzimidazol-5-ylcarbonyl)-piperidine (XII)

5-Benzimidazolecarboxylic acid is coupled to 1,2,3,6-tetrahydropyridine by activation of the acid with carbonyl diimidazole in CH$_2$Cl$_2$ plus 10% (v/v) dimethylformamide. Purification is achieved by chromatography on silica gel. FABMS m/z 455 (parent dimer +1), 228 (parent +1), and 145.

Example XII

Preparation of 1-(quinoxalin-6-ylcarbonyl)-1,2,3,6-tetrahydropyridine (XIII)

3,4-Diaminobenzoic acid (2.0 g; 13 mmol) is dispersed into 50 ml absolute ethanol. To the chocolate-brown slurry is added 2.2 g (15 mmol) of glyoxal (40% in water) that has been dissolved in 10 ml of ethanol. The mixture is stirred at room temperature for 24 hr. The light sand-brown 6-quinoxalinecarboxylic acid is collected by filtration and washed with ethanol and diethyl ether. EMIS m/z=174 (base), 157, 147, 129, and 120.

6-Quinoxalinecarboxylic acid (320 mg; 1.8 mmol) is suspended in 10 ml methylene chloride. As the suspension is stirred, 2 equivalents of triethylamine are added, followed by 0.22 ml (1.8 mmol) of trimethylacetyl chloride. After 15 min, 164 ul (1.8 mmol) of 1,2,3,6-tetrahydropyridine is added and the solution is stirred overnight. The solution is diluted with 20 ml of diethyl ether and washed with 10 ml water followed by 10 ml 10% $NaCO_3$. The organic solution is dried over $Na_2SO_4/K_2CO_3$ and concentrated to a red-brown oil. Purification by chromatography on silica gel (eluted with $CCl_4/CHCl_3$ 1:1) gives a pale yellow oil that eventually solidifies. The solid is layered with hexane and finely dispersed by mechanical crushing to yield pale yellow XIII. EMIS m/z=239 (parent), 157 (base), and 129. $^1H$ NMR δ 2.22 and 2.34 (br, 2), 3.54, 3.94, 3.97, and 4.29 (br, 4), 5.5–6.0 (br, 2), 7.85 (dd, 1, J=8.7, 1.3 Hz), 8.15 (d, 1, J=1.6 Hz), 8.18 (br d, 1, J=8.5 Hz), and 8.90 ppm (s, 1).

Example XIII

Preparation of 1-(quinoxalin-6-ylcarbonyl)-piperidine (XIV)

The coupling of 6-quinoxalinecarboxylic acid to piperidine is accomplished in a manner similar to that used for the preparation of Invention Compound XIII, or by any other method known in the art for activation of aromatic carboxylic acids, such as, for example, activation by carbonyl diimidazole. $^1H$ NMR δ 1.56 and 1.73 (br, 6), 3.40 (br s, 2), 3.79 (br s, 2), 7.82 (dd, 1, J=8.8, 1.9 Hz), 8.13 (d, 1, J=1.6 Hz), 8.17 (d, 1, 8.6 Hz), and 8.9 ppm (m, 2).

Example XIV

In Vitro Physiological Testing

The physiological effects of invention compounds can be tested in vitro with slices of rat hippocampus as follows. Excitatory responses (field EPSPs) are measured in hippocampal slices which are maintained in a recording chamber continuously perfused with artificial cerebrospinal fluid (ACSF). During the 15 minute interval indicated by the horizontal bar in FIG. 1, the perfusion medium is switched to one containing either 1.5 mM aniracetam (left panel) or 750 μM of Invention Compound I (right panel). Responses collected immediately before (1) and at the end of drug perfusion (2) are shown as superimposed inserts in FIG. 1 (calibration bars: horizontal 10 milliseconds, vertical 0.5 mV). The y-axis of the main graph shows the area of the response before, during and after drug perfusion, expressed as percent of the baseline value; and each data point represents a single response.

To conduct these tests, the hippocampus was removed from anesthetized, 2 month old Sprague-Dawley rats and in vitro slices (400 micrometers thick) were prepared and maintained in an interface chamber at 35° C. using conventional techniques [see, for example, Dunwiddie and Lynch, J. Physiol. Vol. 276: 353–367 (1978)]. The chamber was constantly perfused at 0.5 ml/min with ACSF containing (in mM): NaCl 124, KCl 3, $KH_2PO_4$ 1.25, $MgSO_4$ 2.5, $CaCl_2$ 3.4, $NaHCO_3$ 26, glucose 10 and L-ascorbate 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activate a population of the Schaffer-commissural (SC) fibers which arise from neurons in the subdivision CA3 and terminate in synapses on the dendrites of CA1 neurons. Activation of these synapses causes them to release the transmitter glutamate. Glutamate binds to the postsynaptic AMPA receptors which then transiently open an associated ion channel and permit a sodium current to enter the postsynaptic cell. This current results in a voltage in the extracellular space (the field excitatory postsynaptic potential or field "EPSP") which is recorded by a high impedance recording electrode positioned in the middle of the stratum radiatum of CA1.

Figure 1A:
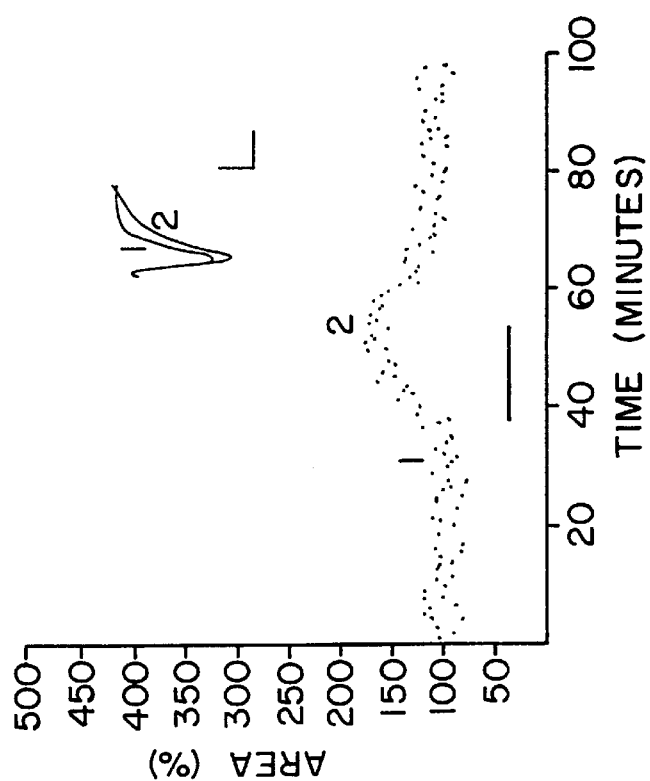

For the experiments summarized in FIG. 1, the intensity of the stimulation current was adjusted to produce half-maximal EPSPs (typically about 1.5–2.0 mV). Paired stimulation pulses were given every 40 sec with an interpulse interval of 200 msec (see below). The field EPSPs of the second response were digitized and analyzed to determine amplitude, half-width, and response area. If the responses were stable for 15–30 minutes (baseline), test compounds were added to the perfusion lines for a period of about 15 minutes. The perfusion was then changed back to regular ACSF.

Paired-pulse stimulation was used since stimulation of the SC fibers, in part, activates interneurons which generate an inhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 milliseconds and using the second ("primed") response for data analysis.

The field EPSP recorded in field CA1 after stimulation of CA3 axons is known to be mediated by AMPA receptors: the receptors are present in the synapses [Kessler et al., Brain Res. Vol. 560: 337–341 (1991)] and drugs that selectively block the receptor selectively block the field EPSP [Muller et al., Science, supra]. Aniracetam increases the mean open time of the AMPA receptor channel and as expected from this increases the amplitude of the synaptic current and prolongs its duration [Tang et al. Science, supra]. These effects are mirrored in the field EPSP, as reported in the literature [see, for example, Staubli et al., Psychobiology supra; Xiao et al., Hippocampus supra; Staubli et al., Hippocampus Vol. 2: 49–58 (1992)]. The same can be seen in the superimposed EPSP traces of FIG. 1 (left hand panel) which were collected before (1) and immediately after (2) the infusion of 1.5 mM aniracetam. The drug augmented the amplitude of the response and extended the duration of the response. The latter effect is responsible for most of the increase in the area (net current) of the response which is plotted in the main graph as a function of time before, during, and after drug infusion. In these tests, as in the published literature, aniracetam has a rapid onset following infusion, and reverses quickly upon washout.

The right hand panel of FIG. 1 summarizes a typical experiment with Invention Compound I used at 750 μM (i.e., one half the concentration of aniracetam). The invention compound produced the same qualitative effects as aniracetam as shown in field EPSPs collected immediately before and immediately after a 15 minute infusion. As is evident upon inspection of the data in FIG. 1, the magnitude of the effects was much greater even though the concentration of invention compound used was only 50% of that of aniracetam. The same can be seen in the main graph (FIG. 1, right hand panel), which shows the effects of Invention Compound I on the area of the field EPSPs as a function of time. Invention compound is similar to aniracetam in that it effected a rapid onset of action and was fully reversible upon washout. Comparison of the two panels in FIG. 1 illustrates the extent to which 750 μM of Invention Compound I was more potent than 1.5 mM aniracetam.

Example XV

Generation of Dose-response Curves and Derived $EC_{50}$ Values for Invention Compounds and Aniracetam Invention Compounds I ((1-(1,4-benzodioxan-5-ylcarbonyl)-1,2,3,6-tetrahydropyridine), II (1-(1,3-benzodioxol-5-ylcarbonyl)-piperidine), III (1-(1,3-benzodioxol-5-ylcarbonyl)-1,2,3,6-tetrahydropyridine), and aniracetam were assayed in the physiological test system described for the generation of data presented in FIG. 1. The response corresponding to an increase of 85% was assumed. The variables set forth in the table refer to the following generic structure:

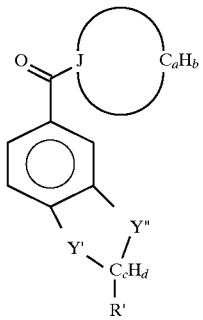

| Compound #* | Y' | Y" | J | a | b | c | d | R' | $EC_{50}$ (mM) |
|---|---|---|---|---|---|---|---|---|---|
| aniracetam | O | — | N—C(O) | 3 | 6 | 1 | 2 | H | 5 |
| I | O | O | N | 5 | 8 | 2 | 3 | H | 0.5 |
| II | O | O | N | 5 | 10 | 1 | 1 | H | 1.5 |
| III | O | O | N | 5 | 8 | 1 | 1 | H | 0.8 |
| IV | O | O | CH—C(O) | 3 | 6 | 1 | 1 | H | 0.9 |
| V | O | O | N | 5 | 10 | 1 | 1 | $CH_3$ | 1.1 |
| VI | O | O | N | 4 | 8 | 1 | 1 | H | 1.2 |
| VII | O | O | N | 6 | 12 | 1 | 1 | H | 4 |
| VIII | O | O | N | 4 | 6 | 2 | 3 | H | 3 |
| IX | O | N | N | 5 | 8 | 1 | 0 | H | 4 |
| X | O | N | N | 5 | 10 | 1 | 0 | H | 1.3 |
| XI | N | O | N | 5 | 8 | 1 | 0 | H | 3 |
| XII | N | NH | N | 5 | 8 | 1 | 0 | H | 5 |
| XIII | N | N | N | 5 | 8 | 2 | 1 | H | 0.05 |
| XIV | N | N | N | 5 | 10 | 2 | 1 | H | 0.3 |
| XV | $N(CH_3)_2$ | — | N | 5 | 8 | — | — | — | 1.7 |
| XVI | O | O | N—C(O) | 3 | 6 | 1 | 1 | H | 2 |

Figure 2B:
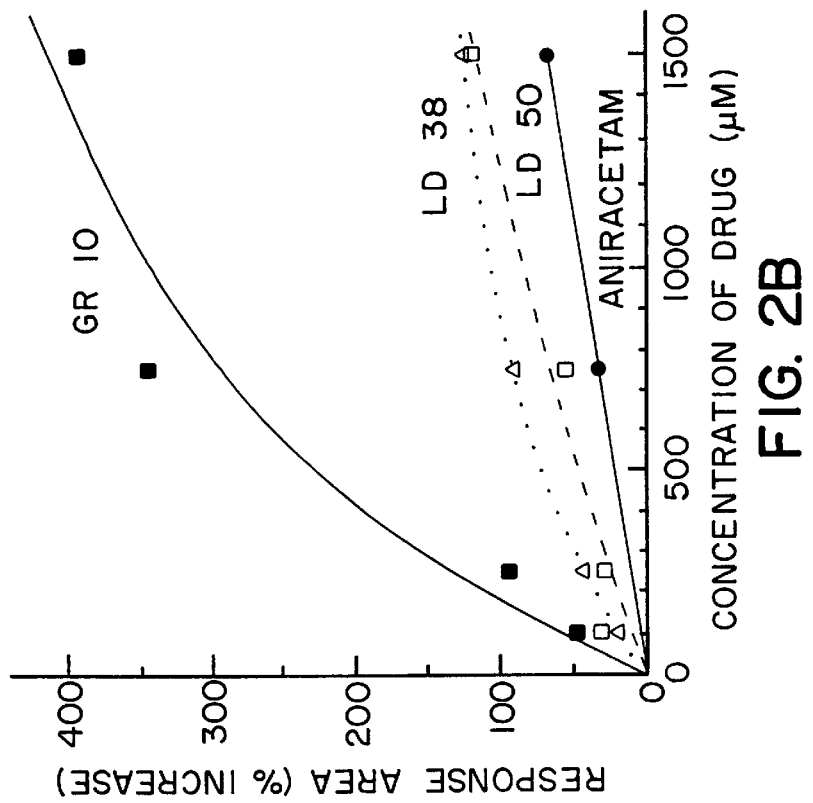
FIG. 2 compares the effects of three invention compounds, i.e., Invention Compound I (i.e., 1-(1,4-benzodioxan-5-ylcarbonyl)-1,2,3,6-tetrahydropyridine), Invention Compound II (i.e., 1-(1,3-benzodioxol-5-ylcarbonyl)-piperidine); alternatively referred to as (N-(3,4-methylenedioxybenzoyl)piperidine, and Invention Compound III (i.e., 1-(1,3-benzodioxol-5-ylcarbonyl)1,2,3,6-tetrahydropyridine; alternatively referred to as N-(3,4-methylenedioxybenzoyl)-1,2,3,6-tetrahydropyridine) with aniracetam across a range of dosages on two response size measures. The invention compounds are seen to be more potent than aniracetam; e.g., at 750 μM, Invention Compound I produces a nine-fold greater increase in the response area than does aniracetam.
Figure 2A:
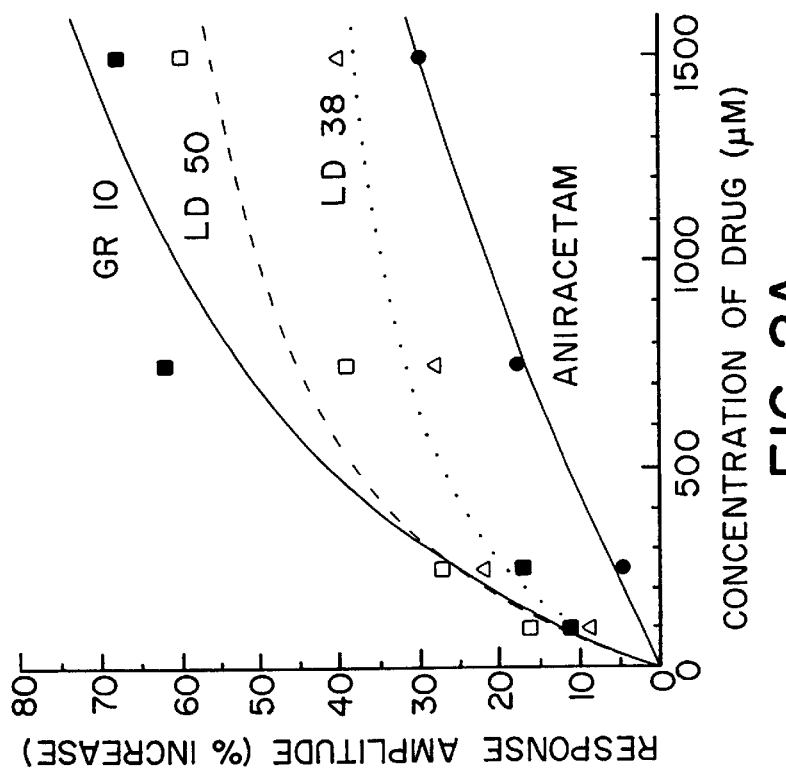

*Compounds I, III–V and VII–XIV were prepared as described above.
Compound II (1-(1,3-benzodioxol-5-ylcarbonyl)-piperidine) and Compound VI (1-(1,3-Benzodioxol-5-ylcarbonyl)-pyrrolidine) are known compounds left panel of FIG. 2 shows the effect of each test compound on the amplitude, while the right panel shows the effect of each test compound on the area of synaptic responses. Each point is the mean of 2–10 independent determinations. The regression lines were calculated assuming a standard hyperbolic saturation function.

The invention compounds produced dose-dependent increases in both measures (i.e., in maximum amplitude and response area) and were effective at concentrations as low as 100 μM. Invention Compound I at this dose enhanced the area of the field EPSP by 46±16% (mean and S.D. of 4 experiments). As readily seen upon inspection of FIG. 2, each of the three invention compounds was significantly more potent than aniracetam at all dosages tested. For example, Invention Compound I (tested at dosages in the range of 750 μM to 1.5 mM) produced a 6–9 times greater effect on response area than did aniracetam at the same concentrations.

The percent increase in field EPSP amplitude was determined for a variety of Invention Compounds, and aniracetam, as described above, and used to construct log dose/response curves in order to estimate $EC_{50}$ values for each compound. $EC_{50}$ values are presented in the following table. Where maximal responses could not be obtained due to limited solubility of some of the compounds, a maximal

Example XVI

Promotion of Long-term Potentiation by Invention Compounds

Figure 3:
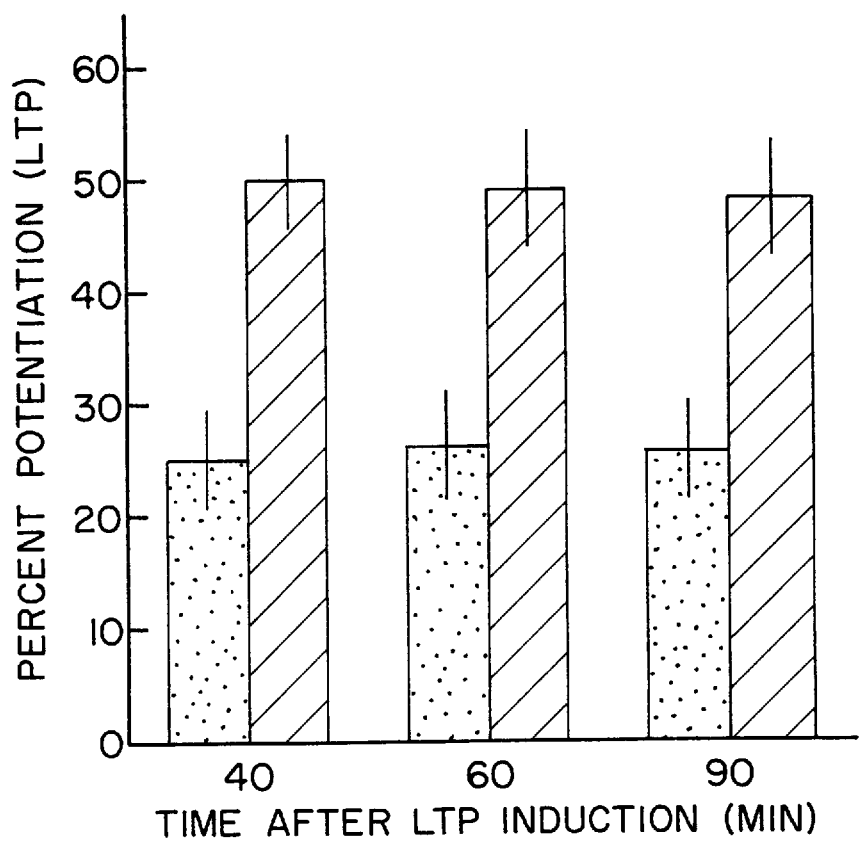
FIG. 3 shows that Invention Compound I increases the magnitude of long-term potentiation (induced by a standard physiological induction paradigm) over that obtained in the absence of the compound.

Long-term potentiation (LTP; a stable increase in the EPSP size of single responses after brief periods of high frequency stimulation) was elicited in the CA1 field of hippocampal slices in the absence (see FIG. 3, stippled bars, N=6) and in the presence of 1.5 mM of Invention Compound I (see FIG. 3, striped bars, N=5). In the latter case, the amount of potentiation was determined after washing out the test compound and comparing the response size with that before test compound infusion. Data presented in FIG. 3 show the percent increase in the EPSP amplitude (mean and S.D.) at 40, 60, and 90 minutes after LTP induction.

For these studies, field EPSPs in slices of hippocampus were elicited by single stimulation pulses and recorded by extracellular electrodes as described in Example II. After collecting responses every 40 seconds for 20–30 minutes to establish a baseline, LTP was induced with ten short bursts of pulses delivered to the CA3 axons; each burst consisted of four pulses separated by 10 milliseconds; the interval between the bursts was 200 milliseconds. This pattern of axon stimulation mimics a discharge rhythm observed in the hippocampus of animals engaged in learning and is referred to as the "theta burst stimulation paradigm" [see, for example, Larson and Lynch in Science Vol. 232: 985–988

(1986)]. Testing with single pulses (one every 40 seconds) is then carried out for an additional 60–90 minutes to determine the amount of stable potentiation in the EPSP amplitude. As shown in FIG. 3, the two second long period of burst stimulation (i.e., 10 bursts separated by 200 milliseconds) increased the size of the field EPSPs in control slices (stippled bars) by about 25%. The increase in the EPSP size was stable for the duration of the recording (90 min in the experiments shown in FIG. 3). Equivalent experiments in rats with chronically implanted electrodes have shown that the increase in EPSP size lasts for as long as stable recordings can be maintained, typically on the order of weeks [see Staubli and Lynch, in Brain Research 435: 227–234 (1987)]. This phenomenon is referred to in the literature as long-term potentiation (LTP).

To determine the effect of test compound on the induction of LTP, 1.5 mM of Invention Compound I was infused for 15 minutes prior to application of theta burst stimulation. Test compound was then washed out until the EPSP half-width (which is changed by test compound, but not by LTP) had returned to its pre-treatment level. The amplitude of the field EPSPs was then compared to that observed before infusion of test compound and burst stimulation to determine the amount of LTP. The striped bars in FIG. 3 summarize the results (mean and S.D.) of five experiments. As is evident upon inspection of FIG. 3, the degree of stable long-term potentiation produced by burst stimulation applied in the presence of Invention Compound I was nearly twice as large as that induced by the same stimulation administered in the absence of the drug (p<0.02).

There is much evidence linking long-term potentiation to memory encoding. Therefore, the data summarized in FIG. 3 provide grounds for predicting that Invention Compound I will be effective in intact animals as a memory enhancer.

Example XVII

Figure 4:
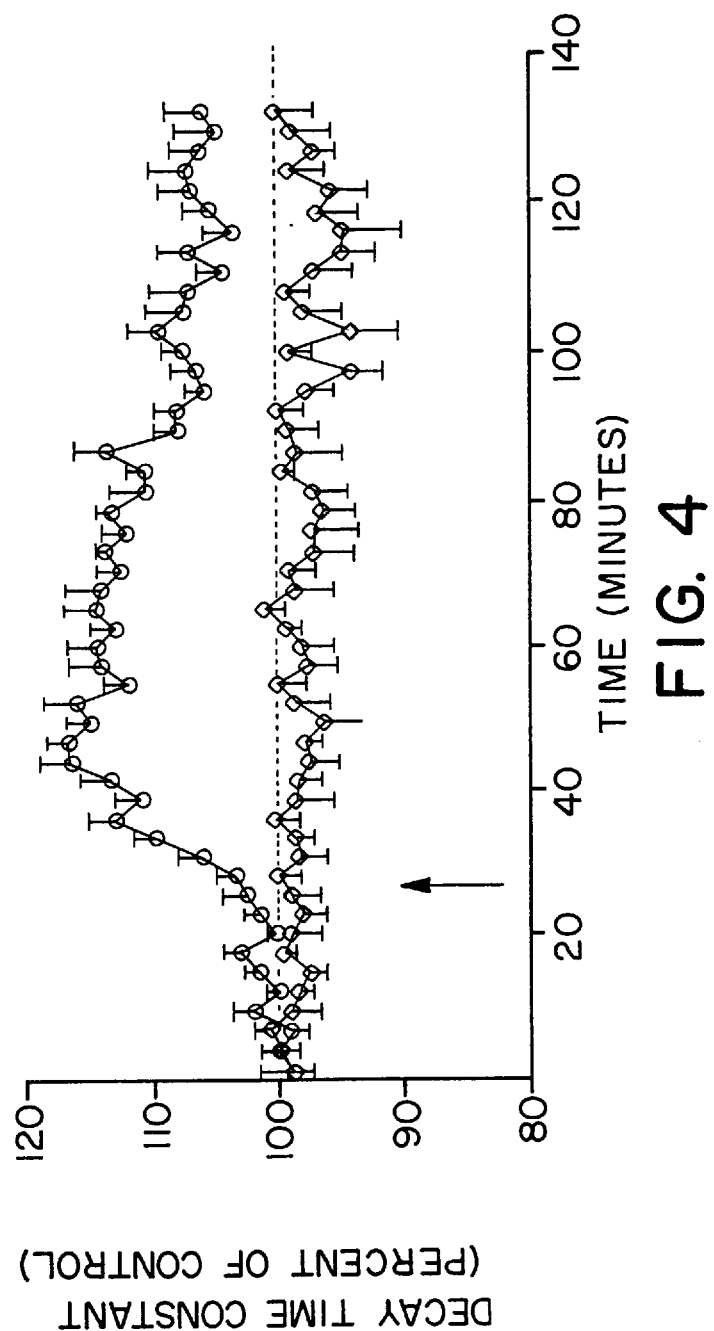
FIG. 4 shows that Invention Compound I slows the decay rate of synaptic responses (a measure of the response duration) recorded in the hippocampal field CA1 of intact rats following peripheral administration of the compound. Data for eight rats injected intraperitoneally with Invention Compound I are compared with results from seven rats injected with the carrier vehicle.

Effect of Intraperitoneally Injected Invention Compound I on Monosynaptic EPSP Responses in the Rat Hippocampus Stimulating and recording electrodes were placed in the hippocampus of anesthetized rats so as to activate and monitor the same synaptic responses as in the slice studies described in Example XV. FIG. 4 shows the size of the normalized decay time constant of the response (mean±S.E.M.) before and after a single intraperitoneal injection (arrow) of Invention Compound I (circles, n=8) or cyclodextrin/saline vehicle (diamonds, n=7). The time constant for the decay of the EPSP is a measure for the duration of the response.

In these experiments, male Sprague-Dawley rats were anesthetized with urethane (1.7 g/kg) and body temperature was maintained at 37° C. with the use of a heat lamp. A stimulation electrode (two twisted stainless steel wires, 150 $\mu$m diameter, insulated with teflon) was placed stereotaxically in the trajectory of the Schaffer collateral (SC) pathway from CA3 to CA1 of the hippocampus (coordinates relative to Bregma: 3.5 mm P., 3.5 mm L., and 3.0–3.7 mm V). A recording electrode (stainless steel, 150 $\mu$m diameter, insulated with teflon) was placed in the ipsilateral CA1 field (coordinates relative to Bregma: 3.8 mm P., 2.9 mm L., and 2.2–2.8 mm V.), 100–200 $\mu$m ventral to the electrophysiologically-identified CA1 stratum pyramidale (i.e., in the stratum radiatum).

Negative field potentials reflecting dendritic EPSPs evoked by SC stimulation (0.1 ms pulses, 10–100 $\mu$A) with paired pulses (inter-pulse interval of 200 msec; see methodology described in Example XV) were amplified 500 times and digitized by computer at 20 sec intervals throughout each experiment. Test compound (120–180 mg/kg of Invention Compound I in 20% w/v 2-hydroxypropyl-beta-cyclodextrin in 50% saline vehicle) or vehicle (1.5–2.1 g/kg) injections were made i.p. Stable synaptic responses for 10–60 min before and 60–180 min after injection were obtained in all animals used for the analysis shown in FIG. 4. The time course of the decay time constant was plotted since the prolongation of EPSP was the most prominent effect of Invention Compound I in hippocampal slices. Decay time constants were determined by single exponential fits to the decay phase of the synaptic response and expressed as a percent of the value obtained during the pre-injection control period.

As is evident from inspection of FIG. 4, the test compound produced a rapid increase in the duration of the synaptic response, and this effect reversed within 60–120 minutes of the injection. The effect of Invention Compound I was somewhat larger for the second (primed) response of the paired stimulation. The effect on response duration is typical for this group of compounds (cf. responses 1 and 2 in the right panel of FIG. 1). Other manipulations which have been used in slices to modulate synaptic responses in general had little effect on the decay time constant [see, for example, Xiao et al. (1991) supra]. These results indicate that sufficient amounts of the test compound cross the blood-brain barrier to augment AMPA receptor functioning in situ, and that test compound influences the response in much the same way as low doses of Invention Compound I directly applied to hippocampal slices. The on-going hippocampal electroencephalogram was continuously monitored in these experiments and in no case did injections of Invention Compound I produce electrographic seizures.

Example XVIII

Distribution of Invention Compound II after Intraperitoneal Injection

To be effective, nootrophic drugs, or their active metabolites, must pass the blood brain barrier or be introduced directly through the blood brain barrier. To test the ability of invention compounds to pass the blood-brain barrier, Invention Compound II was labelled with carbon-11.

Radiolabelled Invention Compound II (see the table above) is synthesized by the following scheme (wherein the numbers in parenthesis refer to the quantity of reagent used, in millimoles):

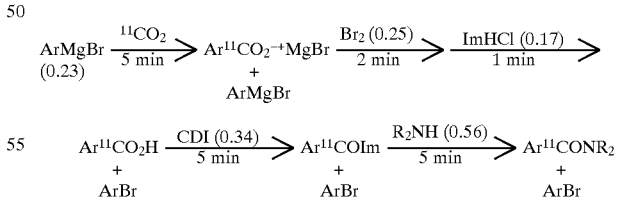

wherein Ar is aryl (such as methylenedioxybenzene), Im is imidazole (thus, ImHCl is imidazole hydrochloride), and R is an alkyl or alkylene radical (so that $R_2NH$ is, for example, piperidine). $^{11}C$-labelled $CO_2$ is produced by cyclotron irradiation and subsequently used in the above-described synthetic scheme. The time to complete the synthesis is about 22 min (2 times the half-life of carbon-11). After purification of [$^{11}C$]II on $C_{18}$ Sep Pak, 260 $\mu$Ci was diluted with 20 mg of nonradioactive II as carrier in a 1-ml solution of 23% propylene glycol and 10% ethanol in physiologically-buffered saline in order to simulate the dosage of 100 mg/Kg that was used in behavioral studies. The final 1 ml of solution was administered to a 200 g rat under halothane anesthesia (1.4–1.7% in oxygen) by intraperitoneal (i.p.) injection.

Figure 5:
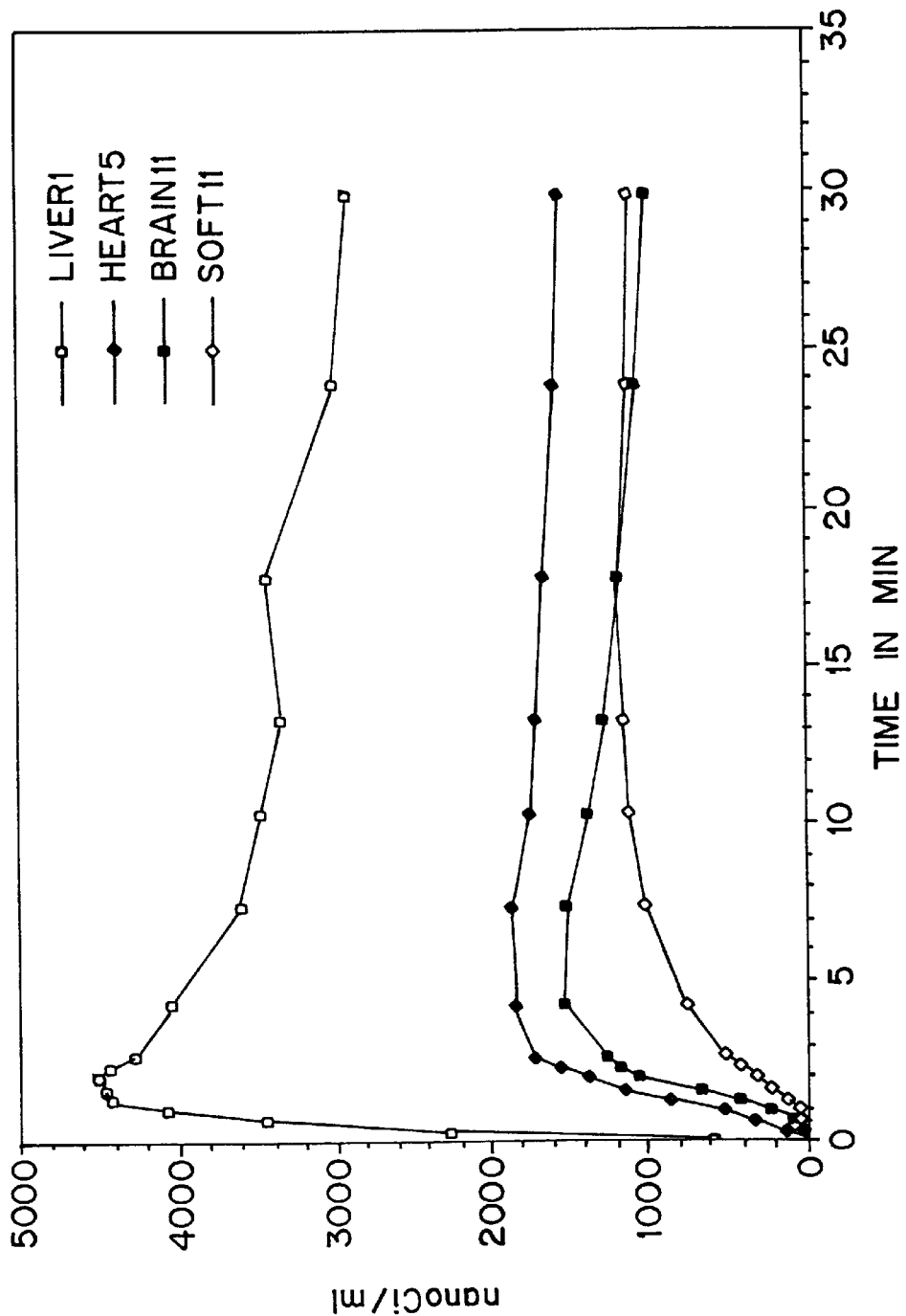
FIG. 5 shows the distribution measured by PET scan of $^{11}C$-labelled Invention Compound II in an appropriate carrier in a 200 gram rat after ip injection. Brain uptake is observed to plateau in 5–10 minutes at a distribution approximately one-quarter that of liver, two-thirds that of heart, and approximately equal to that of the head excluding the cranial cavity.

Biodistribution of the radiotracer in the body of the rat was monitored by a positron camera (Scanditronix PC2048-15B) and the time-activity curves were constructed using a Vax 3500 (Digital Equipment Corporation) and shown in FIG. 5. Four regions of interest were selected: a) liver, upper curve (□); b) heart, second curve from top (♦); c) "soft" or muscle tissue, third curve from top at 30 min (◇); d) brain, bottom curve (■).

The results presented in FIG. 5 indicate that uptake in liver peaked about 3 minutes after injection, uptake in heart and brain peaked about 5 minutes after injection and uptake in soft tissues peaked about 17 minutes after injection. Levels in the liver declined markedly for the first 5 minutes after peaking and then more gradually. Levels in the other three tissues declined very gradually after peaking.

Not surprisingly, liver showed the maximum uptake, followed by heart. Of particular importance is the fact that uptake in the brain was nearly as effective as uptake in the heart, and as much as a quarter that of liver. This demonstrates that Invention Compound II passes freely through the blood-brain barrier.

Further, entry of Invention Compound II into its target tissue was relatively rapid and stayed in the brain for an extended period. These properties indicate that invention compounds may be administered shortly before they are needed, and that frequent readministration may not be necessary.

The invention has been described in detail with reference to particular embodiments thereof. It will be understood, however, that variations and modifications can be effected within the spirit and scope of the invention.

We claim:

1. A compound having the structure:

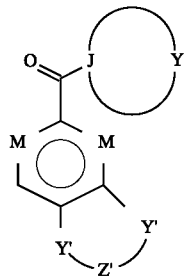

wherein:

is selected from:

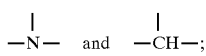

—Y— is selected from:

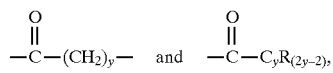

wherein y is 3, 4, or 5; and
—$(CR_2)_x$— and —$C_xR_{(2x-2)}$—, wherein x is 4, 5, or 6;
—R is hydrogen or a straight chain or branched chain alkyl group having 1–6 carbon atoms;
each —M— is independently selected from:
  —C(H)— and
  —C(Z)—, wherein Z is selected from: —R and —OR;
each —Y'— is independently selected from:
  —O—,
—Z'— is selected from:
  —$(CR_2)_z$—, wherein z is 1, 2, or 3, and
  —$C_{z'}R_{(2z'-1)}$—, wherein z' is 1 or 2, or
  —$C_2R_2$—
with the proviso that:
  if each M is —C(H)—, each Y' is —O— and Z' is —$(CR_2)_z$—, wherein R is H, methyl or ethyl then Y is not —$(CH_2)_{4,5}$—.

2. A compound according to claim 1 wherein —Y— is

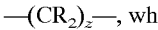

and y is selected from 3 or 4.

3. A compound according to claim 2 wherein Z' is —$CH_2$—.

4. A compound according to claim 1 wherein —Y— is —$(CR_2)_x$—, and x is selected from 4 or 5.

5. A compound according to claim 1 wherein Z' is selected from —$CR_2$—, —$CR_2$—$CH_2$—, or —CR═CH—, wherein each R is independently H or a straight chain or branched chain alkyl group having 1–6 carbon atoms.

6. A compound having the structure:

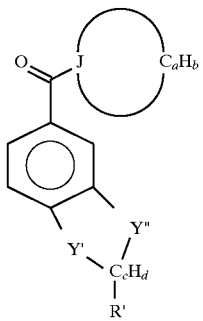

wherein:

is

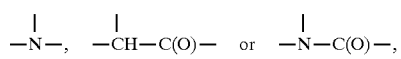

Y' is O,
Y" is O,

R' is H or a straight chain or branched chain alkyl group having 1–4 carbon atoms, a=3, 4, 5 or 6, b=an even number between 6–12, inclusive, depending on the value of a, c=1 or 2, d=0, 1 or 3, or the combination of Y' and $C_cH_d$—R' produces a dialkylamino derivative thereof, wherein a dialkylamino group replaces the heterocyclic ring fused to the core aromatic ring.

7. A compound according to claim 6 wherein

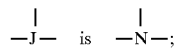

—Y'— and —Y"— are both —O—; a is 5; b is 10; c is 1; d is 1; and R' is —$CH_3$.

8. A formulation useful for enhancing synaptic responses mediated by AMPA receptors, said formulation comprising:

a compound according to claim 1, and a pharmaceutically acceptable carrier.

9. A method for the treatment of a subject to enhance synaptic response mediated by AMPA receptors, said method comprising administering to said subject an effective amount of a compound according to claim 1.

10. A method according to claim 9 wherein the performance of said subject is improved on sensory-motor problems or cognitive tasks dependent upon brain networks utilizing AMPA receptors, wherein the strength of memory encoding by said subject is improved, or wherein brain functioning is improved in subjects with deficiencies in the number of excitatory synapses or in the number of AMPA receptors.

* * * * *